United States Patent
Bourang et al.

(10) Patent No.: US 7,387,639 B2
(45) Date of Patent: Jun. 17, 2008

(54) SHORT SLEEVE STENT DELIVERY CATHETER AND METHODS

(75) Inventors: Henry Bourang, Turlock, CA (US); Udayan G. Patel, San Jose, CA (US); Gil M. Vardi, Town and Country, MO (US); Sepehr Fariabi, Newport Coast, CA (US); Eric Williams, Fairfield, CA (US); Javier Sagastegui, Castro Valley, CA (US); Charles Davidson, Winnetka, IL (US)

(73) Assignee: Advanced Stent Technologies, Inc., Pleasanton, CA (US)

( * ) Notice: Subject to any disclaimer, the term of this patent is extended or adjusted under 35 U.S.C. 154(b) by 564 days.

(21) Appl. No.: 09/860,744

(22) Filed: May 18, 2001

(65) Prior Publication Data

US 2002/0173835 A1 Nov. 21, 2002

Related U.S. Application Data

(63) Continuation-in-part of application No. 09/663,111, filed on Sep. 15, 2000, which is a continuation-in-part of application No. 09/614,472, filed on Jul. 11, 2000, now abandoned, which is a continuation-in-part of application No. 09/325,996, filed on Jun. 4, 1999, now abandoned, which is a continuation-in-part of application No. 09/455,299, filed on Dec. 6, 1999, now Pat. No. 6,692,483.

(51) Int. Cl.
*A61F 2/82* (2006.01)

(52) U.S. Cl. ..................................... 623/1.11

(58) Field of Classification Search ............... 623/1.11, 623/1.23, 1.35; 606/108; 128/898
See application file for complete search history.

(56) References Cited

U.S. PATENT DOCUMENTS

| 5,749,825 | A  * | 5/1998 | Fischell et al. .............. 600/3 |
| 5,755,734 | A  * | 5/1998 | Richter et al. ............ 606/194 |
| 6,190,353 | B1 | 2/2001 | Makower et al. |
| 6,203,568 | B1 | 3/2001 | Lombardi et al. |
| 6,210,429 | B1 | 4/2001 | Vardi et al. |
| 6,346,089 | B1 | 2/2002 | Dibie |
| 6,540,779 | B2 | 4/2003 | Richter et al. |
| 6,596,020 | B2 | 7/2003 | Vardi et al. |

(Continued)

FOREIGN PATENT DOCUMENTS

WO WO99/00835 1/1999

*Primary Examiner*—Michael Thaler
(74) *Attorney, Agent, or Firm*—Merchant & Gould P.C.

(57) ABSTRACT

A stent delivery catheter comprises a catheter body having a proximal end, a distal end, and a guidewire lumen extending from the distal end to at least part way between the proximal end and the distal end. A balloon is disposed over the catheter body near the distal end, and a stent is positioned over the balloon. The stent has a proximal end, a distal end, and a side opening between the proximal end and the distal end. A side sheath is coupled to the catheter body and has a proximal end, a distal end, and a guidewire lumen extending between the proximal end and the distal end. The proximal end of the side sheath is located between the proximal end of the catheter body and the balloon, and the side sheath exits out of the side opening of the stent.

22 Claims, 7 Drawing Sheets

U.S. PATENT DOCUMENTS

| | | |
|---|---|---|
| 6,599,315 B2 | 7/2003 | Wilson |
| 6,884,258 B2 | 4/2005 | Vardi et al. |
| 6,955,687 B2 | 10/2005 | Richter et al. |
| 6,955,688 B2 | 10/2005 | Wilson et al. |
| 6,962,602 B2 | 11/2005 | Vardi et al. |

* cited by examiner

SHORT SLEEVE STENT DELIVERY CATHETER AND METHODS

CROSS-REFERENCES TO RELATED APPLICATIONS

This application is a continuation-in-part of U.S. patent application Ser. No. 09/325,996, filed Jun. 4, 1999, entitled "CATHETER WITH SIDE SHEATH," the disclosure of which is herein incorporated by reference. This application claims priority to 09/325,996 to the extent appropriate by law.

This application also is a continuation-in-part of U.S. patent application Ser. No. 09/455,299, filed Dec. 6, 1999, entitled "CATHETER WITH ATTACHED FLEXIBLE SIDE SHEATH," the disclosure of which is herein incorporated by reference. This application claims priority to 09/455,299 to the extent appropriate by law.

This application also is a continuation-in-part of U.S. patent application Ser. No. 09/614,472, filed Jul. 11, 2000, entitled "CATHETER WITH SIDE SHEATH," which is a continuation-in-part of said 09/325,996, and which is a continuation-in-part of said 09/455,299. The disclosure of said 09/614,472 is herein incorporated by reference. This application claims priority to 09/614,472 to the extent appropriate by law.

This application also is a continuation-in-part of U.S. patent application Ser. No. 09/663,111, filed Sep. 15, 2000, entitled "CATHETER WITH SIDE SHEATH AND METHODS," which is a continuation-in-part of said 09/455,299 and of said 09/614,472. The disclosure of said 09/663,111 is herein incorporated by reference. This application claims priority to 09/663,111 to the extent appropriate by law.

BACKGROUND OF THE INVENTION

As described in related U.S. patent application Ser. No. 08/744,002 filed Nov. 4, 1996 (now abandoned); Ser. No. 09/007,265 filed Jan. 14, 1998, which issued on Apr. 3, 2001 as U.S. Pat. No. 6,210,429; Ser. No. 08/935,383 filed Sep. 23, 1997 (now abandoned); Ser. No. 60/088,301 filed Jun. 5, 1998, now expired; Ser. No. 09/663,111, filed Sep. 15, 2000, and Ser. No. 09/794,740, filed Feb. 26, 2001; and PCT Patent Application Publication No. WO 99/36002, filed Jan. 13, 1998; systems and methods have been developed for deploying a main stent in a main vessel at the intersection of a main vessel and a branch vessel. Further, a branch stent may optionally be positioned within a branch vessel through a side opening in the main stent. The complete disclosures of all these references are herein incorporated by reference.

When using multiple guidewires to introduce a catheter system through body lumens, one condition that may occur is known as "wire crossing". In such cases, the guidewires over which the catheter system is advanced intertwine within the guide catheter and vasculature. This condition may prevent the successful delivery of the catheter system by impeding its travel and, subsequently, the alignment of the stent's side opening with the ostium of the branch vessel.

This invention relates to other novel techniques and delivery systems for deploying stents at vessel intersections to permit the side opening to be aligned with the ostium of the branch vessel, among other features. Some embodiments are particularly directed toward managing the guidewires used to introduce the catheter systems to the region of interest. Some embodiments are also directed toward facilitating easy introduction and removal of catheter systems.

SUMMARY OF THE INVENTION

In one embodiment, the invention provides an exemplary stent delivery catheter that may be employed to deliver a stent to a particular region of interest within a patient's vasculature. In some cases, the delivery catheter may not include a stent and may be used in other procedures, such as conventional balloon angioplasty.

The catheter comprises a catheter body having a proximal end, a distal end, and a guidewire lumen extending from the distal end to at least part way between the proximal end and the distal end. For example, the guidewire lumen may extend fully to the proximal end, or may terminate in a side opening anywhere proximal to an accompanying stent to provide the catheter with side or short exchange capabilities. In one aspect, the side opening may be within about 1 cm to about 150 cm of the distal end. A balloon is disposed over the catheter body near the distal end, and in some embodiments a stent positioned over the balloon. The stent in one embodiment has a proximal end, a distal end, and a side opening between the proximal end and the distal end. A side sheath is coupled to the catheter body and has a proximal end, a distal end, and a guidewire lumen extending between the proximal end and the distal end. The proximal end of the side sheath is located at some point proximal to the balloon. In one aspect, the side sheath may pass through the proximal end of the stent and exit out of the side opening.

The use of the shortened side sheath provides a number of significant advantages. For example, shorter guidewires may be used to introduce the catheter. For example, guidewires ranging from about 100 cm to about 200 cm, and more preferably about 150 cm, may be used instead of conventional 300 cm guidewires. In this way, the catheter may be introduced and withdrawn from the patient by a single worker. Another significant feature is that the overall profile of the catheter is reduced to allow the catheter to be introduced into smaller guide catheters, thereby reducing trauma to the patient. For example, the catheter profile may be as low as about 4 to 7 French. The smaller profile also permits the catheter to be more easily maneuvered and rotated during introduction to the patient. For example, the reduction is profile permits the catheter to be introduced adjacent to a backup guidewire in the main vessel. If any wire crossing occurs between the back up guidewire and the branch vessel guidewire, the catheter may more easily be torqued by the physician to overcome the wire crossing.

In one aspect, the side sheath extends out of the side opening by a distance of at least about 0 cm to about 7 cm, and the catheter body has a length in the range from about 50 cm to about 150 cm. In another aspect, the catheter body further includes a balloon inflation lumen that is in fluid communication with the balloon. For example, the balloon inflation lumen may be coaxially disposed about the guidewire lumen. Conveniently, a hub may be coupled to the distal end to facilitate balloon inflation and guidewire introduction.

In a further aspect, the catheter body includes at least one radiopaque marker near the balloon, and the side sheath includes at least one radiopaque marker near the distal end. In this way, separation of the markers may be observed to indicate that the side sheath has advanced into the branch vessel.

In one particular embodiment, the catheter body guidewire lumen terminates at the proximal end. Alternatively, the catheter body guidewire lumen may terminate in a side port within the catheter body at a location anywhere proximal to the balloon. For example, the side port may be located within about 1 cm to about 150 cm of the distal end. In this way, the overall profile of the catheter may be further reduced, with both the branch vessel guidewire and the main vessel guidewire may extend along the outside of the catheter body. Such a configuration further provides short or side exchange capabilities for the catheter. Reduction in profile size may be accomplished, for example, by constructing the catheter body from a tubular member, such as a hypo tube, surrounded by a nylon jacket. A stiffening mandrel may also be incorporated into a distal portion of the catheter body to provide torquing capabilities.

In embodiments where no stent is used, a second balloon may be provided on side sheath. In this way, the catheter may be used in "kissing the balloon" procedures where the balloons are simultaneously inflated into two separate vessels.

The invention further provides an exemplary method for placing a stent having a side hole into a main vessel such that the side hole is aligned with an ostium of a branch vessel that extends from the main vessel. Conveniently, the method may utilize a catheter similar to the catheter previously described. When using such a catheter, a branch vessel guidewire is introduced into the main vessel until a distal end of the branch vessel guidewire passes into the branch vessel, and a primary main vessel guidewire is introduced through the catheter body guidewire lumen. The catheter containing the primary main vessel guidewire is introduced over the branch vessel guidewire such that the branch vessel guidewire passes through the side sheath. The catheter is advanced over the branch vessel guidewire until the side sheath is within the branch vessel and the side opening of the stent is aligned with an ostium of the branch vessel. At this point, the balloon may be inflated to deploy the stent.

By advancing the catheter over a single guidewire, i.e., the branch vessel guidewire, the problem of wire crossing is significantly reduced. After the side sheath is near or into the branch vessel, the primary main guidewire may be further advanced into the main vessel.

In some cases, a physician will not want to lose wire placement and will therefore desired to maintain a guidewire within the main vessel at all times. In such cases, a secondary or back up main vessel guidewire may be inserted into the main vessel such that a distal end of the secondary main vessel guidewire passes beyond the ostium of the branch vessel prior to inserting the catheter over the branch vessel guidewire. Once the catheter is near the ostium and the primary main vessel guidewire has been advanced through the catheter, the secondary main vessel guidewire may be withdrawn prior to inflation of the balloon. If the branch vessel guidewire and the secondary main vessel guidewire cross, the catheter body may be torqued during insertion in order to overcome the wire crossing. The wire crossing may be overcome since the secondary main vessel guidewire runs along side of the catheter. Since the profile of the catheter may be relatively small, maneuvering of the catheter within the patient is also facilitated.

After withdrawing the secondary main vessel guidewire, the catheter may be further advanced over the branch vessel guidewire and the primary main vessel guidewire to align the side opening in the stent with the ostium. After the stent has been deployed, the balloon may be deflated, and the catheter may be withdrawn from the main vessel and the branch vessel. Conveniently, the catheter body may include at least one marker and the side sheath may also include at least one marker. With this configuration, separation of the markers may be observed fluoroscopically to indicate that the catheter body has passed beyond the ostium and the side member extends into the branch vessel. In one aspect, the primary main vessel guidewire distally extends typically about 1 cm to about 3 cm from the catheter body while the catheter is being advanced over the branch vessel guidewire. In another aspect, the catheter is advanced over the branch vessel guidewire until the balloon exits a guiding catheter. At that point, the primary main vessel guidewire may be extended further into the main vessel.

In one particular aspect, the catheter body guidewire lumen terminates in a side port within the catheter body at a location within about 1 cm to about 150 cm of the distal end. With such a configuration, the primary main vessel guidewire is routed through the guidewire lumen in the catheter body until exiting through the side port.

The catheters described above may be introduced to the region of interest using other techniques as well. For example, both the branch vessel guidewire and the main vessel guidewire may initially be placed into the branch and main vessels, respectively. The catheter may then be routed over both guidewires. As another example, the branch and main vessel guidewires may both be preloaded into the catheter. The preloaded catheter may then be advanced through the main vessel until exiting the guiding catheter. At this point, the branch vessel guidewire may be advanced through the side sheath and into the branch vessel, and the main vessel guidewire may be advanced through the catheter body and further into the main vessel. With the guidewires in place, the catheter may be advanced into position in a manner similar to that previously described.

DESCRIPTION OF THE SPECIFIC EMBODIMENTS

Figure 1:
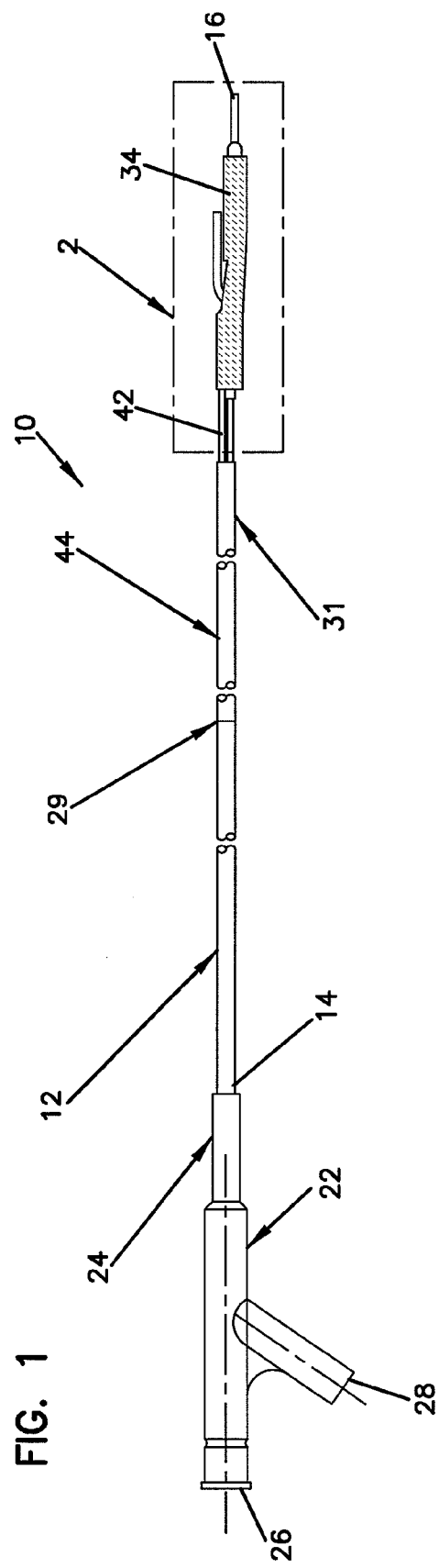
FIG. 1 is a side view of one embodiment of a delivery catheter according to the invention.

In one aspect, the invention provides systems and methods for deploying stents at a vessel bifurcation such that a cell in the stent that is specifically designed to function as a branch aperture (referred to herein as a side hole of the stent) is in registry with the ostium of the branch vessel. Further, various techniques are provided for managing the guidewires over which the stents and stent delivery catheters are directed. More specifically, the invention provides techniques to help prevent the crossing of guidewires or to traverse crossed guidewires when introducing catheters used to deploy stents or other devices that require advancement over multiple guidewires, where it is important for the guidewires to be tangle free and parallel with respect to each other. In this way, the catheters may more easily be introduced to the diseased region.

The invention also provides techniques for reducing the profile of such delivery catheters, and to facilitate the introduction, withdrawal and exchange of such catheters. In one aspect, the invention provides catheters that may be used with shorter guidewires so that they are useful with short or side exchange techniques.

Applications of the invention include the cardiac, coronary, renal, peripheral vascular, gastrointestinal, pulmonary, urinary and neurovascular systems and the brain.

Advantages of the invention include, but are not limited to, the use of an improved stent delivery apparatus, which may deliver stents to: 1) completely cover the bifurcation point of bifurcation vessels; 2) be used to treat lesions in one branch of a bifurcation while preserving access to the other branch for future treatment; 3) allow for differential sizing of the stents in a bifurcated stent apparatus even after a main stent is implanted; 4) treat bifurcation lesions in a bifurcated vessel where the branch vessel extends from the side of the main vessel; and 5) be marked with, or at least partly constructed of, material which is imageable by commonly used intraluminal catheterization visualization techniques including but not limited to ultrasound or x-ray.

Some catheters and techniques of the invention may be used with non-stent applications. For example, the introduction techniques may be used with a wide variety of catheter designs that may be used to simultaneously inflate two balloons (to prevent a "snowplowing" effect), to prevent injury during introduction, and the like.

As described herein, a side hole in the main vessel stent refers to specific cell of the stent, which form a relatively large opening and which is intended to be aligned with the ostium of the branch vessel. Such a side hole is separate from any of the multiple passageways extending through the side of the stent between struts in the stent geometry. Accordingly, the side hole in the stent is a hole, which is understood to be larger than other passages through the stent, except the longitudinal bore of the stent itself. Additionally the side hole of the stent is configured such that a central axis extending perpendicularly through the side hole is generally perpendicular to the longitudinal axis of the stent. In some aspects, this side hole is defined by a band of continuous material, which outlines the perimeter of the side hole. This continuous band of material preferably comprises serpentine patterns over its length so that the area of the side hole expands together with the expansion of the stent. In various aspects, the continuous band comprises protrusions, which project inwardly from a peripheral edge of the side opening and, when expanded, deflect perpendicularly to the longitudinal axis of the stent. Preferably, these protrusions (or expandable portions) are initially aligned within a cylindrical envelope of the tubular body of the stent.

In one embodiment, the invention provides an elongate catheter body having a lumen through which a guidewire may be inserted. The guidewire lumen begins at a distal end and may terminate at the proximal end or somewhere between the proximal end and the distal end. A shorter catheter body is attached to or integrally formed with the longer catheter body. The shorter catheter body also includes a guidewire lumen. The two catheter bodies separate at their distal ends, and one of the catheter bodies includes a balloon near the distal end and a balloon inflation lumen is provided to inflate the balloon. In this way, a stent with a side opening may be crimped over the balloon, with the distal end of the other catheter body passing between the stent and the balloon, and exiting out of the side opening. The shorter catheter body preferably terminates within about 1 cm to about 150 cm of the balloon.

The use of the shorter catheter body permits the catheter to be used with shorter guidewires. For example, guidewires ranging from about 100 cm to about 200 cm, and more preferably about 150 cm, may be used instead of conventional 300 cm guidewires. In this way, the catheter may be introduced and withdrawn from the patient by a single worker because the shorter catheter body proximally extends only a short distance over the guidewire after initial loading. Another significant feature is that the overall profile of the catheter is reduced to allow the catheter to be introduced into smaller guide catheters, thereby reducing trauma to the patient. For example, the catheter profile may be as low as about 4 to 7 French. The smaller profile also permits the catheter to be more easily maneuvered and rotated during introduction to the patient. In this way, the side opening may easily be radially aligned with the ostium of the branch vessel because the catheter may turn itself into radial alignment during insertion. As another example, if the catheter is inserted next to a back up guidewire in the main vessel, the catheter may more easily be torqued by the physician to overcome any wire crossing with the back up guide wire. Such a catheter may conveniently be advanced over a single guidewire, or over a pair of guidewires.

The invention further provides an exemplary technique for introducing a catheter having two guidewire lumens to a vessel bifurcation. Although well suited for catheters having a shortened catheter body relative to the other catheter body, it will be appreciated that the techniques may be used with any catheter having two guidewire lumens for receiving parallel guidewires. The technique preloads one of the guidewires that is to remain within the main vessel into one of the guidewire lumens. The distal end of this guidewire may extend typically about 1 cm to about 3 cm beyond the distal end of the catheter body. The other guidewire is inserted into the main vessel until a distal end extends into the branch vessel. The preloaded catheter is then inserted over the branch vessel guidewire and advanced through the main vessel. When the catheter body is near the vessel bifurcation, the preloaded guidewire is advanced out of the catheter body and further into the main vessel beyond the vessel bifurcation. The catheter may then be advanced over both guidewires until the one of the catheter bodies is within the branch vessel. If desired, a backup main vessel guidewire may be positioned within the main vessel prior to introduction of the catheter. When using three guidewires, any of the techniques described in copending U.S. application Ser. No. 09/794,740, filed Feb. 26, 2001, previously incorporated by reference, may also be used.

Figure 2:
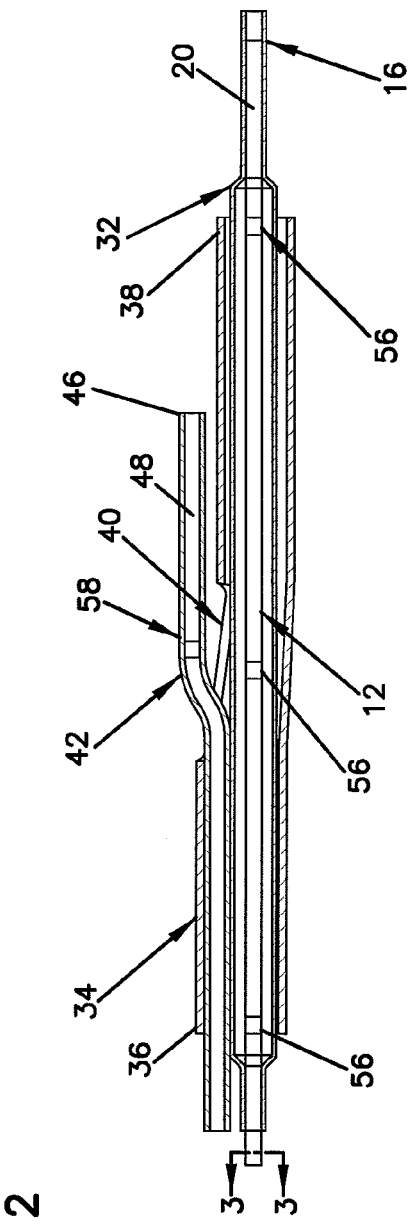
FIG. 2 is a cross sectional enlarged view of a section 2 of the catheter of FIG. 1.
Figure 3:
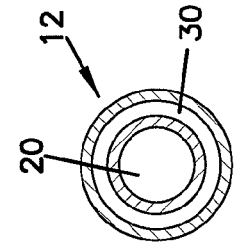
FIG. 3 is a cross sectional enlarged view of a section 3—3 of the catheter of FIG. 2.

Referring now to FIG. 1, one embodiment of a delivery catheter 10 will be described. Catheter 10 comprises a catheter body 12 having a proximal end 14 and a distal end 16. As best shown in FIG. 2, a guidewire lumen 20 extends between proximal end 14 and distal end 16. Catheter body 12 functions as a main shaft and is constructed of a relatively stiff material, such as a polyamide, PEEK, stainless steel hypotubes or the like to provide torquability to the catheter body. Proximal end 14 is coupled to an inflation/deflation hub 22 having a strain relief portion 24. Hub 22 further includes a guidewire exit port 26 which leads to guidewire lumen 20, and a balloon inflation port 28. At a bond joint 29, a length of dual lumen tubing 31 is coupled. As best shown in FIG. 3, one of these lumens is a coaxial lumen and includes a balloon inflation lumen 30 that is coaxially disposed about guidewire lumen 20. Balloon inflation port 28 is in fluid communication with balloon inflation lumen 30.

Disposed about a distal portion of catheter body 12 is a balloon 32 that is in fluid communication with balloon inflation lumen 30. In this way, balloon 32 may be inflated and deflated from port 28 as is known in the art. Loaded onto balloon 32 is a stent 34 having a proximal end 36, a distal end 38 and a side opening 40. Stent 34 is radially expanded during inflation of balloon 32 in order to deploy stent 34 within a vessel.

Coupled to catheter body 12 is a side sheath 42 that has a proximal end that terminates in an exit port 44 and a distal end 46. A guidewire lumen 48 extends between exit port 44 and distal end 46. As shown best in FIG. 2, side sheath 42 passes through proximal end 36 and exits out of side opening 40. Distal end 46 may extend about 0.1 cm to about 7 cm out of side opening 40 to facilitate entry of side sheath 42 into a branch vessel.

Side sheath 42 is attached to catheter body 12 at some point proximal to balloon 32 so that the rest of side sheath 42 is unattached and free to be manipulated. Side sheath 42 may be integrally formed with catheter body 12 where attached, or may be separated secured, such a with a bonding material, with a sleeve, or the like. Exit port 44 is preferably within about 1 cm to about 150 cm of balloon 32, more preferably within about 1 cm to about 15 cm, and most preferably within about 1 cm to about 5 cm. With such a configuration, a branch vessel guidewire that is used facilitate alignment of side opening 40 with an ostium of a branch vessel may extend along side catheter body 12. In this way, the overall size of catheter 12 may be reduced. Further, such a configuration may be used to improve guidewire management, such as when loading the catheter with guidewires, when manipulating the catheter to overcome a wire crossing, when using three guidewire introduction techniques, and the like. Another advantage of such a design is the simplification of hub 22 that only includes two ports. Such a part may more easily be injection molded and requires leak testing for only two ports.

Figure 4:
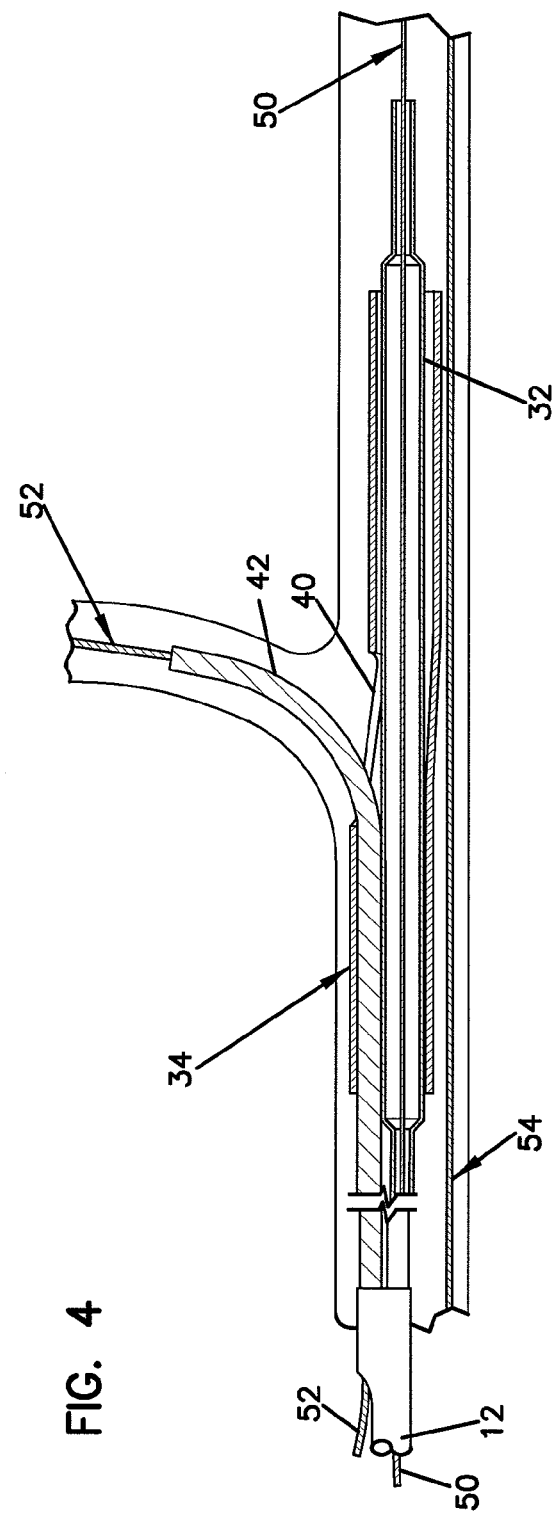
FIG. 4 illustrates a distal portion of the catheter of FIG. 2 when introduced to a bifurcated vessel using a three guidewire technique according to the invention.

Referring also now to FIG. 4, a distal portion of catheter 10 is shown at the location of a vessel bifurcation. A main vessel guidewire 50 extends through guidewire lumen 20 and into the main vessel beyond the bifurcation. A branch vessel guidewire 52 extends through guidewire lumen 48 and into the branch vessel. Because of the reduced profile, a backup guidewire 54 may also be positioned in the main vessel alongside of catheter 10 and will be described in greater detail hereinafter.

As best shown in FIG. 2, catheter body 12 includes a set of radiopaque markers 56, and side sheath 42 also includes a radiopaque marker 58. Markers 56 and 58 may be used to facilitate angiographic visualization of catheter 10 to insure proper placement of stent 34. For example, when in the position shown in FIG. 4, marker 58 separates relative to markers 56 to indicate that side sheath 42 has successfully reached the branch vessel, thereby aligning side opening 40 with the ostium of the branch vessel.

Figure 5:
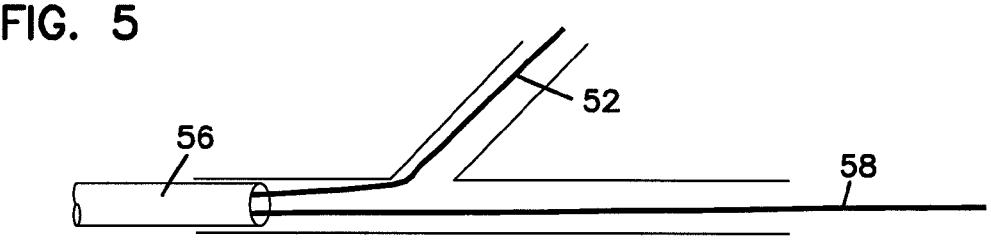
FIGS. 5 through 9 schematically illustrate a technique for deploying a stent using the catheter of FIG. 1.

Referring now to FIGS. 5–9, one method for delivering stent 34 using catheter 10 will be described schematically. Initially, a guide catheter 56 is introduced to extend past the aortic arch as in known in the art. A backup main vessel guidewire 58 is inserted through catheter 56 and beyond the vessel bifurcation as shown in FIG. 5. Branch vessel guidewire 52 is also inserted through catheter 56 and into the branch vessel.

Figure 6:
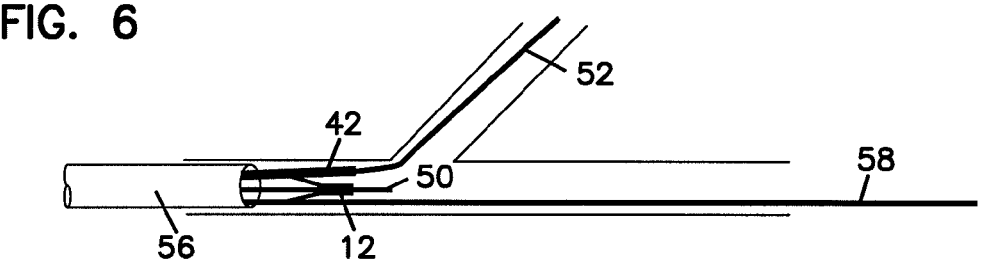
Figure 7:
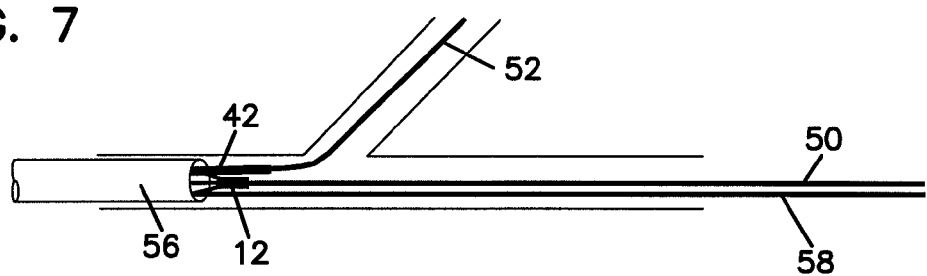
Figure 8:
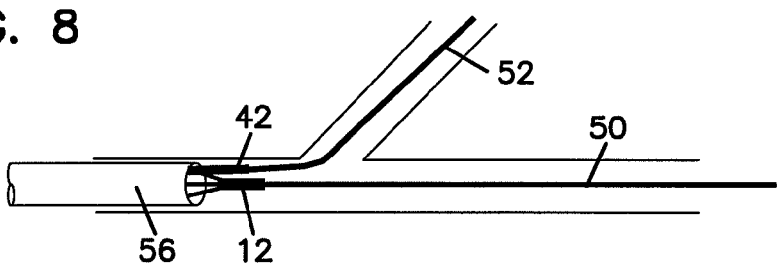

As shown in FIG. 6, main vessel guidewire 50 is introduced through catheter body 12 until extending about 1 to 3 cm beyond catheter body 12 to preload catheter 10. When preloaded, branch vessel guidewire 52 is routed through side sheath 42, and then catheter 10 is advanced through guide catheter 56 over guidewire 52. Conveniently, this may be done using short or side exchange techniques and shorter guidewires since guidewire 52 may be grasped by the caregiver as soon as it exits port 44. Once exiting guide catheter 56, guidewire 50 is advanced out of catheter body 12 and further into the main vessel as shown in FIG. 7. The backup guidewire 58 is then withdrawn as shown in FIG. 8.

Figure 9:
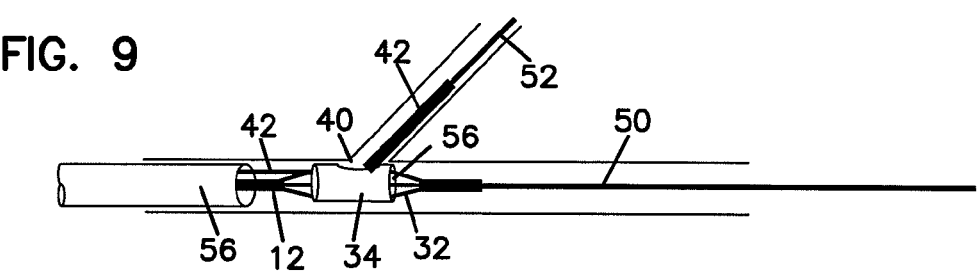

Catheter 10 is then advanced over both guidewires 50 and 52 under fluoroscopic visualization until side sheath 42 is within the branch vessel and side opening 40 is aligned with the ostium. Balloon 32 is then inflated to deploy stent 34, with side opening 40 being aligned with the ostium as shown in FIG. 9. Balloon 32 may then be deflated and catheter 10 removed from the patient.

By preloading catheter 10 onto guidewire 50, catheter 10 may be inserted over a single guidewire, i.e., guidewire 52. In this way, no guidewire crossing occurs between guidewires 50 and 52. Further, if guidewires 52 and 58 cross, catheter 10 may be torqued and manipulated to force catheter 10 past the wire crossing. This is possible because guidewire 58 is exterior to catheter 10.

Although shown with backup guidewire 58, it will be appreciated that the method of FIGS. 5 through 9 may be performed without backup guidewire 58. In this way, essentially no wire crossing will occur.

Figure 10:
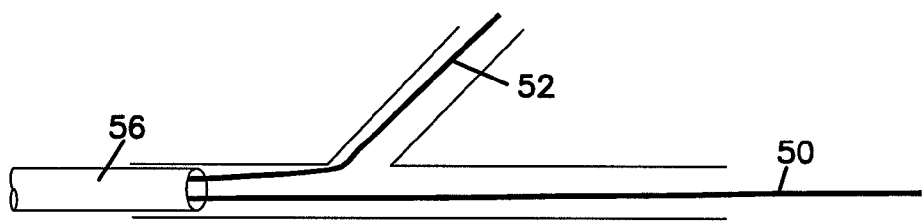
FIGS. 10 through 12 schematically illustrate another technique for deploying a stent using the catheter of FIG. 1.
Figure 11:
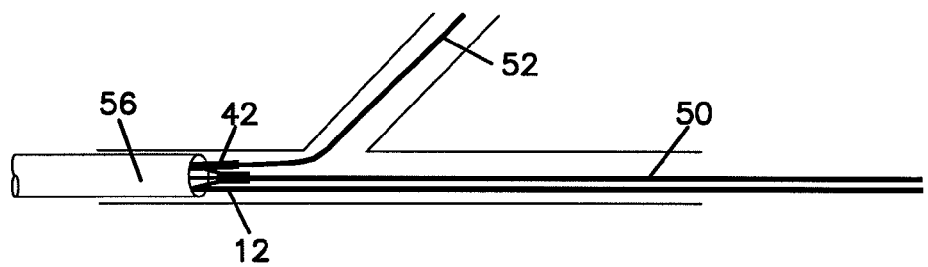
Figure 12:
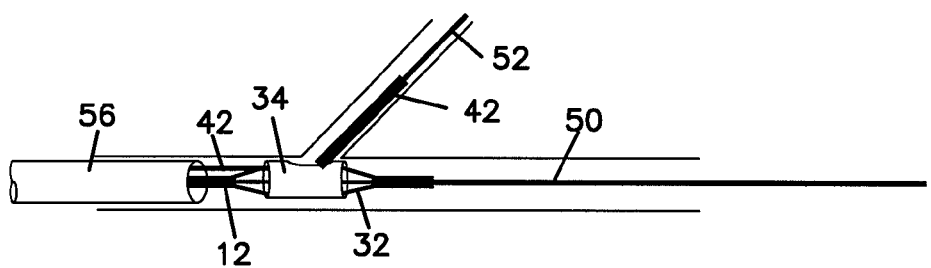

Shown in FIGS. 10 through 12 is an alternative method for deploying stent 34 using catheter 10. As shown in FIG. 10, main vessel guidewire 50 is inserted through catheter 56 and past the branch vessel. Branch vessel guidewire 52 is also inserted through catheter 56 and into the branch vessel. Catheter 10 is then loaded onto guidewires 50 and 52 while outside the patient, with guidewire 50 passing through catheter body 12 and guidewire 52 passing through side sheath 42. Catheter 10 is advanced over guidewires 50 and 52 under angiographic imaging until side opening 40 of stent 34 is aligned with the branch vessel as shown in FIGS. 11 and 12. Balloon 32 may then be inflated to deploy stent 34. After deployment balloon 32 is deflated and catheter 10 is removed from the patient.

Figure 13:
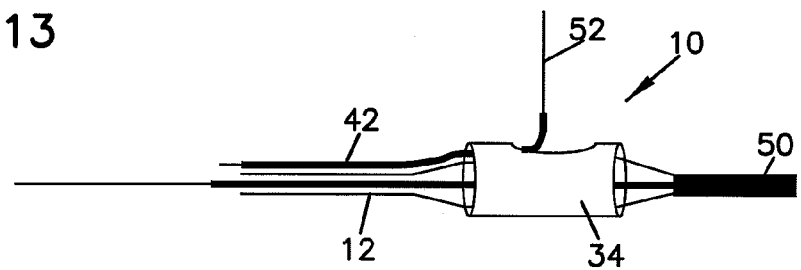
FIGS. 13 through 16 schematically illustrate still another technique for deploying a stent using the catheter of FIG. 1.
Figure 14:
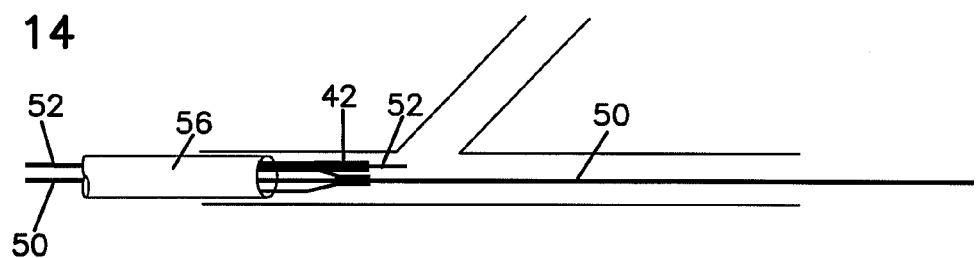
Figure 15:
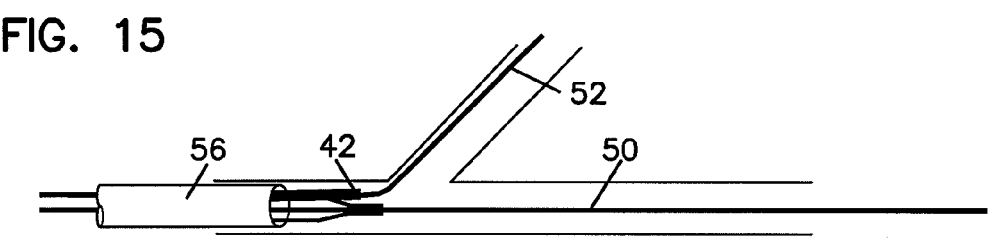
Figure 16:
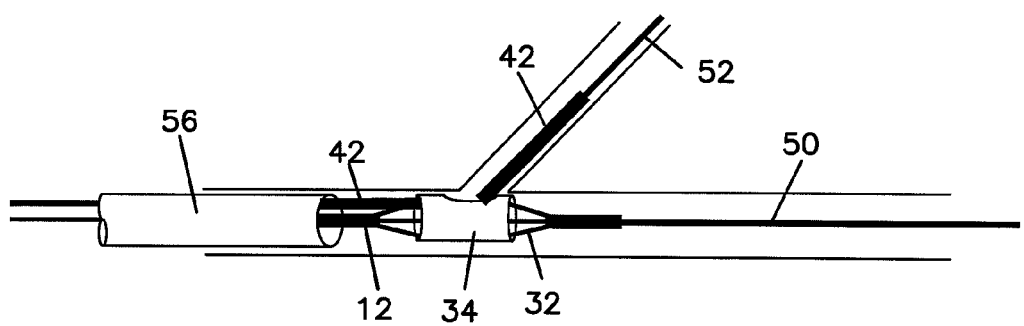

FIGS. 13 through 16 illustrate still another method for deploying stent 34 using catheter 10. As shown in FIG. 13, catheter 10 is preloaded onto guidewires 50 and 52, with guidewire 50 extending through catheter body 12 and guidewire 52 extending through side sheath 42. Guidewires 50 and 52 may extend about 1 to about 3 cm. Preloaded catheter 10 is then introduced through guide catheter 56 (which was previously inserted) and shown in FIG. 14. When the distal ends of guidewires 50 and 52 reach or are near to the vessel bifurcation (which corresponds to the mouth of guide catheter 56), guidewires 50 and 52 are extended from catheter 10 until guidewire 10 is further within the main vessel and guidewire 52 is within the branch vessel as shown in FIG. 15. Catheter 10 is advanced over guidewires 50 and 52 under angiographic imaging until side opening 40 of stent 34 is aligned with the branch vessel as shown in FIG. 16. Balloon 32 may then be inflated to deploy stent 34. After deployment balloon 32 is deflated and catheter 10 is removed from the patient.

Figure 17:
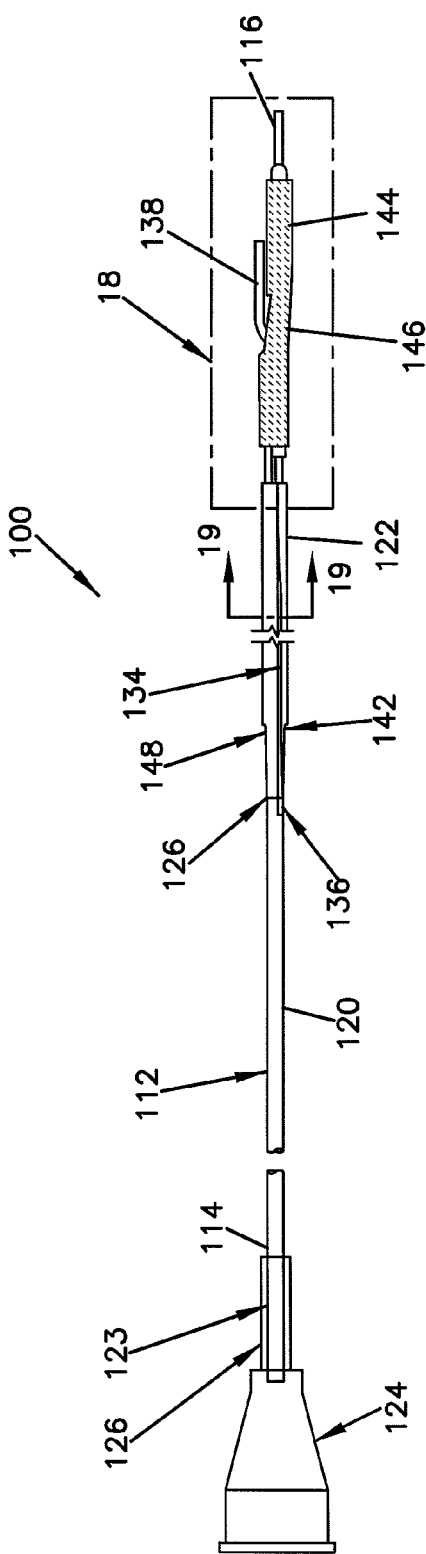
FIG. 17 is a side view of another embodiment of a delivery catheter according to the invention.
Figure 18:
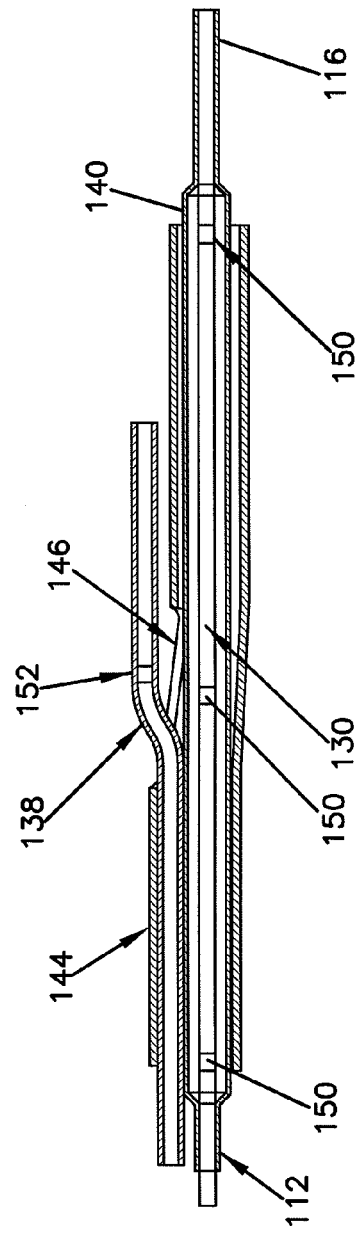
FIG. 18 is a cross sectional enlarged view of a section 18 of the catheter of FIG. 17.
Figure 19:
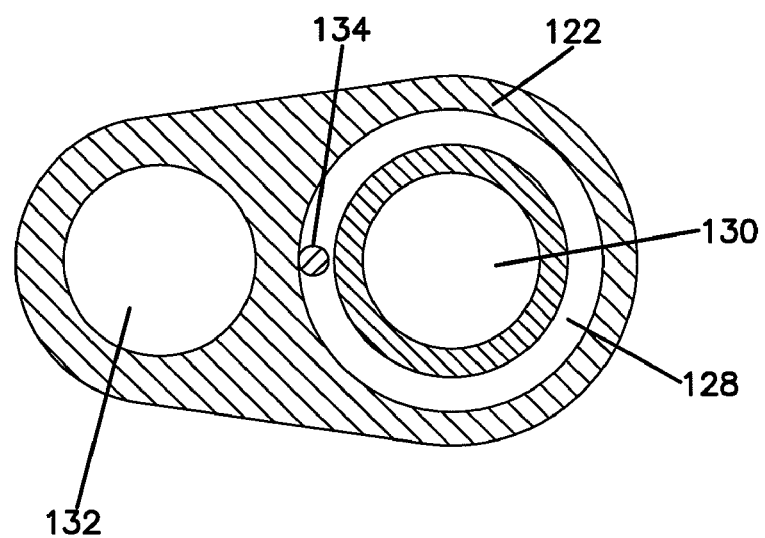
FIG. 19 is a cross sectional view of the catheter of FIG. 17 taken along lines 19—19.

FIGS. 17 through 19 show another embodiment of a stent delivery catheter 100 that is constructed such that both the main vessel guidewire and the branch vessel guidewire is routed only partially through the catheter to provide a smaller design, to provide dual short or side exchange capabilities and to permit the use of shorter guidewires, as well as other features previously described in connection with catheter 10. Catheter 100 comprises a catheter body 112 having a proximal end 114 and a distal end 116. Catheter body 112 may conveniently be divided into a proximal portion 120 and a distal portion 122. Proximal portion 120 may be constructed of a hypo tube 123 and be connected to an inflation/deflation hub 124 having a strain relief portion 126. Proximal portion 120 is coupled to distal portion 122 at a joint bond 126.

As best shown in FIG. 19, distal portion 122 comprises a length of dual lumen tubing having a balloon inflation lumen 128 that is coaxially disposed about a guidewire lumen 130. Also included is a side sheath guidewire lumen 132. Disposed within lumen 128 is a tapered stiffening mandrel 134 to provide rigidity and torquability to distal portion 122. Mandrel 134 is connected to proximal portion 120 at a weld point 136.

As best shown in FIGS. 17 and 18, the dual length tubing of distal portion 122 separates into two separate lengths of tubing, one of which is conveniently identified as a continuation of catheter body 112, and the other being identified as a side sheath 138 which includes lumen 132. Coupled to catheter body 112 near distal end 116 is a balloon 140 that is in fluid communication with balloon inflation lumen 122 to permit balloon 140 to be inflated and deflated from hub 124. Guidewire lumen 130 continues to distal end 116 and proximally terminates at a side opening 142 that may be located anywhere between hub 124 and balloon 140. In this way, the profile of catheter 100 may be reduced, and side port 142 provides short or side exchange capabilities for the guidewire extending through lumen 130.

Disposed over balloon 140 is a stent 144 having a side opening 146. Side sheath 138 exits side opening 146 in a manner similar to that described with previously embodiments. Also similar to previous embodiments, side sheath 138 proximally terminates in a side port 148 somewhere between hub 124 and balloon 140. In this way, catheter 100 is provided with short or side exchange capabilities for the branch vessel guidewire that extends through side sheath 138 as well as for the main vessel guidewire passing through lumen 130.

In use, catheter 100 may be introduced using any of the techniques previously described in order to deploy stent 144. To facilitate alignment of side opening 146, fluoroscopically visible markers 150 and 152 may be included. These markers separate as side sheath 138 passes into the branch vessel as previously described.

Catheter 100 has the additional feature of side or short exchange guidewire capabilities using side port 142. Since side sheath 138 also has a side exit port, dual short guidewire exchange capabilities are provided. Further, by running both guidewire along side of the catheter, the overall profile may be further reduced to enhance the benefits previously described.

The invention has now been described in detail for purposes of clarity and understanding. However, it will be appreciated that certain changes and modifications may be made within the scope of the appended claims.

What is claimed is:

1. A method for placing a stent having a side hole into a main vessel such that the side hole is aligned with an ostium of a branch vessel that extends from the main vessel, the method comprising:

providing a delivery catheter that comprises a catheter body having a proximal end, a distal end, and a guidewire lumen extending from the distal end to at least part way between the proximal end and the distal end; a balloon disposed over the catheter body near the distal end; a stent positioned over the balloon, the stent having a proximal end, a distal end, and a side opening between the proximal end and the distal end; and a side sheath coupled to the catheter body, the side sheath having a proximal end, a distal end, and a guidewire lumen extending between the proximal end and the distal end, wherein the proximal end of the side sheath is located between the proximal end of the catheter body and the balloon, and wherein the side sheath exits out of the side opening of the stent;

introducing a first guiding apparatus into the main vessel until a distal end of the first guiding apparatus passes into only one vessel;

advancing the catheter over only the first guiding apparatus such that the first guiding apparatus passes through at least a portion of the delivery catheter, until the catheter is in the region of the ostium;

advancing a second guiding apparatus through at least a portion of the delivery catheter so as to provide a guiding apparatus in each vessel;

advancing the catheter over the first guiding apparatus and the second guiding apparatus until the side sheath is within the branch vessel and the side opening of the stent is aligned with an ostium of the branch vessel; and inflating the balloon to deploy the stent.

2. A method as in claim 1, further comprising introducing a secondary main vessel guidewire into the main vessel such that a distal end of the secondary main vessel guidewire passes beyond the ostium of the branch vessel prior to inserting the catheter over the first guiding apparatus, and withdrawing the secondary main vessel guidewire prior to inflation of the balloon.

3. A method as in claim 2, further comprising advancing the catheter over the first guiding apparatus and the second guiding apparatus after the secondary main vessel guidewire has been withdrawn.

4. A method as in claim 2, wherein the catheter body is constructed of a relatively stiff material, and further comprising torquing the proximal end of the catheter body to rotate the catheter body and thereby overcome a wire cross between the first guiding apparatus and the secondary main vessel guidewire.

5. A method as in claim 1, further comprising deflating the balloon and withdrawing the catheter from the main vessel and the branch vessel.

6. The method of claim 1, wherein said first guiding apparatus and said second guiding apparatus are each a guidewire.

7. The method of claim 6, wherein said first guiding apparatus is a branch vessel guidewire.

8. The method of claim 6, wherein said second guiding apparatus is a main vessel guidewire.

9. The method of claim 8, further comprising inserting the main vessel guidewire into the catheter body guidewire lumen prior to the step of advancing the catheter over only the first guiding apparatus, and maintaining a fixed axial position of the main vessel guidewire relative to the catheter body guidewire lumen during the step of advancing the catheter over only the first guiding apparatus.

10. A method as in claim 9, wherein the primary main vessel guidewire distally extends about 1 to about 3 cm from the catheter body while the catheter is being advanced over the first guiding apparatus.

11. A method as in claim 9, wherein the catheter is advanced over the first guiding apparatus until the balloon exits a guiding catheter.

12. A method as in claim 9, wherein the catheter body guidewire lumen terminates in a side port within the catheter body at a location within about 1 cm to about 150 cm of the distal end, and further comprising routing the primary main vessel guidewire through the guidewire lumen in the catheter body until exiting through the side port.

13. A method as in claim 1, wherein the catheter body includes at least one marker and the side sheath includes at least one marker, and further comprising observing separation of the markers to indicate that the catheter body has passed beyond the ostium and the side sheath extends into the branch vessel using angiographic imaging.

14. A method for placing a stent having a side hole into a main vessel such that the side hole is aligned with an ostium of a branch vessel that extends from the main vessel, the method comprising:

providing a delivery catheter that comprises a catheter body having a proximal end, a distal end, and a guidewire lumen extending from the distal end to at least part way between the proximal end and the distal end; a balloon disposed over the catheter body near the distal end; a stent positioned over the balloon, the stent having a proximal end, a distal end, and a side opening between the proximal end and the distal end; and a side sheath coupled to the catheter body, the side sheath having a proximal end, a distal end, and a guidewire lumen extending between the proximal end and the distal end, wherein the proximal end of the side sheath is located between the proximal end of the catheter body and the balloon, and wherein the side sheath exits out of the side opening of the stent;

introducing a main vessel guidewire into the main vessel until a distal end of the main vessel guidewire passes beyond the branch vessel;

introducing a branch vessel guidewire into the main vessel until a distal end of the branch vessel guidewire passes into the branch vessel;

advancing the catheter over the branch vessel guidewire and the main vessel guidewire such that the main vessel guidewire passes through the guidewire lumen of the catheter body and the branch vessel guidewire passes through the side sheath;

advancing the catheter over the main vessel guidewire and the branch vessel guidewire until the side sheath is within the branch vessel and the side opening of the stent is aligned with an ostium of the branch vessel; and inflating the balloon to deploy the stent.

15. A method as in claim 14, further comprising introducing a secondary main vessel guidewire into the main vessel such that a distal end of the secondary main vessel guidewire passes beyond the ostium of the branch vessel prior to inserting the catheter over the branch vessel guidewire, and withdrawing the secondary main vessel guidewire prior to inflation of the balloon.

16. A method as in claim 15, further comprising further advancing the catheter over the branch vessel guidewire and the primary main vessel guidewire after the secondary main vessel guidewire has been withdrawn.

17. A method as in claim 15, wherein the catheter body is constructed of a relatively stiff material, and further comprising torquing the proximal end of the catheter body to rotate the catheter body and thereby overcome a wire cross between the branch vessel guidewire and the secondary main vessel guidewire.

18. A method as in claim 14, further comprising deflating the balloon and withdrawing the catheter from the main vessel and the branch vessel.

19. A method as in claim 14, wherein the catheter body includes at least one marker and the side sheath includes at least one marker, and further comprising observing separation of the markers to indicate that the catheter body has passed beyond the ostium and the side sheath extends into the branch vessel using angiographic imaging.

20. A method as in claim 14, wherein the primary main vessel guidewire is preloaded in the side sheath and distally extends about 1 to about 3 cm from the catheter body while the catheter is being advanced over the branch vessel guidewire.

21. A method as in claim 14, wherein the catheter is advanced over the branch vessel guidewire until the balloon exits a guiding catheter.

22. A method as in claim 14, wherein the catheter body guidewire lumen terminates in a side port within the catheter body at a location within about 1 cm to about 150 cm of the distal end, and further comprising routing the main vessel guidewire through the guidewire lumen in the catheter body until exiting through the side port.

* * * * *

UNITED STATES PATENT AND TRADEMARK OFFICE
CERTIFICATE OF CORRECTION

PATENT NO. : 7,387,639 B2
APPLICATION NO. : 09/860744
DATED : June 17, 2008
INVENTOR(S) : Bourang et al.

Page 1 of 1

It is certified that error appears in the above-identified patent and that said Letters Patent is hereby corrected as shown below:

Col. 11, lines 24-26, claim 14: Delete "introducing a main vessel guidewire into the main vessel until a distal end of the main vessel guidewire passes beyond the branch vessel;"

Col. 11, lines 30-34, claim 14: "advancing the catheter over the branch vessel guidewire and the main vessel guidewire such that the main vessel guidewire passes through the guidewire lumen of the catheter body and the branch vessel guidewire passes through the side sheath;" should read --advancing the catheter over only the branch vessel guidewire such that the branch vessel guidewire passes through the side sheath;--

Col. 14, line 35, claim 14: Insert --advancing the catheter over the branch vessel guidewire until the catheter is in close proximity to the branch vessel;
 inserting a primary main vessel guidewire through the catheter body and further into the main vessel until extending beyond the ostium of the branch vessel;--

Col. 14, lines 35-38, claim 14: "advancing the catheter over the main vessel guidewire and the branch vessel guidewire until the side sheath is within the branch vessel and the side opening of the stent is aligned with an ostium of the branch vessel; and" should read --advancing the catheter over the branch vessel guidewire and the primary main vessel guidewire until the side sheath is within the branch vessel, with the side opening of the stent being aligned with the ostium of the branch vessel, and the catheter body passes further into the main vessel; and--

Signed and Sealed this

Eleventh Day of May, 2010

David J. Kappos
*Director of the United States Patent and Trademark Office*